US009808382B2

(12) United States Patent
Bergstrom et al.

(10) Patent No.: US 9,808,382 B2
(45) Date of Patent: Nov. 7, 2017

(54) ABSORBENT ARTICLE HAVING FLUID FLOW CONTROL MEMBER

(71) Applicant: SCA Hygiene Products AB, Gothenburg (SE)

(72) Inventors: Per Bergstrom, Gothenburg (SE); Charlotte Persson, Gothenburg (SE); Malin Lundman, Gothenburg (SE); Frank Muller, Wiehl (DE); Stefan Muller, Wiehl (DE)

(73) Assignee: SCA HYGIENE PRODUCTS AB, Gothenburg (SE)

( * ) Notice: Subject to any disclaimer, the term of this patent is extended or adjusted under 35 U.S.C. 154(b) by 0 days.

(21) Appl. No.: 14/650,965

(22) PCT Filed: Dec. 28, 2012

(86) PCT No.: PCT/EP2012/005388
§ 371 (c)(1),
(2) Date: Jun. 10, 2015

(87) PCT Pub. No.: WO2014/101927
PCT Pub. Date: Jul. 3, 2014

(65) Prior Publication Data
US 2015/0313771 A1    Nov. 5, 2015

(51) Int. Cl.
*A61M 27/00* (2006.01)
*A61M 39/28* (2006.01)
(Continued)

(52) U.S. Cl.
CPC ...... *A61F 13/539* (2013.01); *A61F 13/53708* (2013.01); *A61F 13/53743* (2013.01);
(Continued)

(58) Field of Classification Search
CPC .................. A61F 13/539; A61F 2013/530481
See application file for complete search history.

(56) References Cited

U.S. PATENT DOCUMENTS

| 5,062,418 A | 11/1991 | Dyer et al. |
| 5,065,600 A | 11/1991 | Byles |
| (Continued) | | |

FOREIGN PATENT DOCUMENTS

| DE | 100 55 902 A1 | 6/2001 |
| DE | 600 34 681 T2 | 1/2008 |
| (Continued) | | |

OTHER PUBLICATIONS

International Search Report (PCT/ISA/210) dated Jul. 16, 2013, by the European Patent Office as the International Searching Authority for International Application No. PCT/EP2012/005389.
(Continued)

*Primary Examiner* — Tatyana Zalukaeva
*Assistant Examiner* — Sara Sass
(74) *Attorney, Agent, or Firm* — Buchanan Ingersoll & Rooney PC

(57) ABSTRACT

An absorbent article, the absorbent article being a personal hygiene article, includes a liquid permeable top sheet, a liquid impermeable back sheet, an absorbent core enclosed between the top sheet and the back sheet, and a fluid flow control member arranged between the top sheet and the backsheet. The fluid flow control member is a spacer fabric having a basis weight of 150-300 gsm and including a top layer, a bottom layer and an interconnecting layer of pile filaments between the top layer and the bottom layer. The pile filaments have a fineness of 80-130 dtex and the density of pile filament connections is 50-150/cm$^2$.

19 Claims, 4 Drawing Sheets

(51) Int. Cl.
*A61M 39/00* (2006.01)
*A61F 13/539* (2006.01)
*A61F 13/537* (2006.01)
*A61F 13/53* (2006.01)

(52) U.S. Cl.
CPC .......... *A61F 2013/530481* (2013.01); *D10B 2401/02* (2013.01); *D10B 2403/021* (2013.01)

(56) References Cited

U.S. PATENT DOCUMENTS

| | | | |
|---|---|---|---|
| 5,356,405 A | 10/1994 | Thompson et al. | |
| 5,589,245 A | 12/1996 | Roell | |
| 5,735,145 A | 4/1998 | Pernick | |
| 5,807,295 A | 9/1998 | Hutcheon et al. | |
| 5,817,391 A | 10/1998 | Rock et al. | |
| 5,938,673 A * | 8/1999 | DePierro | A46B 15/00 606/161 |
| 6,103,641 A | 8/2000 | Gehring, Jr. | |
| 6,151,928 A | 11/2000 | Anyon et al. | |
| 6,755,052 B1 | 6/2004 | Sytz | |
| 7,913,520 B1 | 3/2011 | Chen et al. | |
| 9,072,639 B2 | 7/2015 | Essers | |
| 9,308,138 B2 | 4/2016 | Andersson et al. | |
| 2002/0062113 A1 | 5/2002 | Thomas et al. | |
| 2002/0198508 A1 | 12/2002 | Takatera et al. | |
| 2003/0195487 A1 | 10/2003 | Thomas | |
| 2004/0087927 A1 | 5/2004 | Suzuki | |
| 2004/0097151 A1 | 5/2004 | McMurray | |
| 2004/0168479 A1 | 9/2004 | McMurray | |
| 2005/0148965 A1* | 7/2005 | Richlen | A61F 13/15756 604/367 |
| 2005/0159721 A1 | 7/2005 | Yamamoto et al. | |
| 2005/0238843 A1 | 10/2005 | Schindzielorz et al. | |
| 2006/0019056 A1 | 1/2006 | Turner et al. | |
| 2006/0142717 A1 | 6/2006 | Horowitz | |
| 2007/0059496 A1* | 3/2007 | Russell | A61F 13/5323 428/188 |
| 2007/0212959 A1 | 9/2007 | Johnson | |
| 2008/0020173 A1* | 1/2008 | Fukunaga | D04B 21/04 428/92 |
| 2008/0072627 A1 | 3/2008 | Muller et al. | |
| 2008/0299854 A1 | 12/2008 | Hilleary et al. | |
| 2008/0306462 A1 | 12/2008 | Bruckner et al. | |
| 2009/0076472 A1 | 3/2009 | Goldwasser et al. | |
| 2009/0306616 A1 | 12/2009 | Wennerbäck | |
| 2010/0201020 A1 | 8/2010 | Russell et al. | |
| 2010/0229606 A1 | 9/2010 | Ikenaga et al. | |
| 2010/0249738 A1 | 9/2010 | Tondkar et al. | |
| 2013/0144241 A1 | 6/2013 | Persson et al. | |
| 2015/0313771 A1 | 11/2015 | Bergstrom et al. | |

FOREIGN PATENT DOCUMENTS

| | | |
|---|---|---|
| DE | 10 2008 020 287 B3 | 2/2010 |
| EP | 0841883 B1 | 5/1998 |
| EP | 0 994 207 A1 | 4/2000 |
| EP | 1 486 190 A1 | 12/2004 |
| FR | 2 929 818 A1 | 10/2009 |
| GB | 2 292 526 A | 2/1996 |
| GB | 2504873 A | 2/2014 |
| JP | H04-41753 A | 2/1992 |
| JP | H06-327711 A | 11/1994 |
| JP | 2001-089959 A | 4/2001 |
| JP | 2002-165829 A | 6/2002 |
| JP | 2002-339205 A | 11/2002 |
| JP | 2003-342859 A | 12/2003 |
| JP | 2006-014792 A | 1/2006 |
| JP | 2006-167196 A | 6/2006 |
| JP | 2008-284190 A | 11/2008 |
| JP | 2009-280927 A | 12/2009 |
| JP | 2010-119741 A | 6/2010 |
| RU | 2280427 C2 | 7/2006 |
| RU | 2 414 203 C2 | 3/2011 |
| WO | 97/47263 A1 | 12/1997 |
| WO | 98/33464 A1 | 8/1998 |
| WO | WO 2005/051656 A1 | 6/2005 |
| WO | WO 2009/105000 A1 | 8/2009 |

OTHER PUBLICATIONS

Written Opinion (PCT/ISA/237) dated Jul. 16, 2013, by the European Patent Office as the International Searching Authority for International Application No. PCT/EP2012/005389.

International Search Report (PCT/ISA/210) dated Jul. 16, 2013, by the European Patent Office as the International Searching Authority for International Application No. PCT/EP2012/005388.

Written Opinion (PCT/ISA/237) dated Jul. 16, 2013, by the European Patent Office as the International Searching Authority for International Application No. PCT/EP2012/005388.

Gunter F. Schmidt, "Abstandsgewirke Ohne Und MIT Dekorseite Fur Anwendungen Im Automobil", Melliand Textilberichte, Feb. 28, 1993, pp. 37-39 and 129-134.

International Preliminary Report on Patentability (Form PCT/IB/326, Form PCT/IB373 and Form PCT/ISA237) dated Jun. 30, 2015 for International Application No. PCT/EP2012/005389.

International Preliminary Report on Patentability (Form PCT/IB/326, Form PCT/IB373 and Form PCT/ISA237) dated Jun. 30, 2015 for International Application No. PCT/EP2012/005388.

Davies et al., "The Use of Spacer Fabrics for Absorbent Medical Applications", Journal of Fiber Bioengineering and Informatics, (2009), vol. 1, No. 4, pp. 321-330. (10 pages).

Wollina et al., "Spacer Fabrics—A Potential Tool in the Prevention of Chronic Wounds", Exogenous Dermatology, (2002), vol. 1, No. 6, pp. 276-278. (3 pages).

Office Action dated Nov. 23, 2016, by the U.S. Patent and Trademark Office in the copending U.S. Appl. No. 14/650,951. (15 pages).

Office Communication dated Dec. 7, 2016, by the U.S. Patent and Trademark Office in the copending U.S. Appl. No. 14/650,951. (3 pages).

Decision on Grant dated Nov. 3, 2016, by the Russian Patent Office in corresponding Russian Patent Application No. 2015131102 and an English Translation of the Decision. (16 pages).

Decision on Grant dated Jun. 10, 2016 issued in the corresponding Russian Patent Application No. 2015131108 and English translation (12 pages).

Notice of Reasons for Rejection dated May 30, 2016 issued in the corresponding Japanese Patent Application No. 2015-548216 and English translation (10 pages).

Office Action (Notification of Reasons for Refusal) dated Jul. 15, 2016, by the Japanese Patent Office in corresponding Japanese Patent Application No. 2015-549994 and an English Translation of the Office Action (9 pages).

Office Action dated Apr. 22, 2016, by the U.S. Patent and Trademark Office in the copending U.S. Appl. No. 14/650,951. (14 pages).

Office Action dated Jul. 8, 2016, by the U.S. Patent and Trademark Office in the copending U.S. Appl. No. 14/650,951. (21 pages).

Decision of Rejection dated Mar. 6, 2017 by the Japanese Patent Office in the copending Japanese Patent Application No. 2015-549994 and English translation. (11 pages).

Office Action dated Apr. 3, 2017, by the U.S. Patent and Trademark Office in the copending U.S. Appl. No. 14/650,951. (30 pages).

* cited by examiner

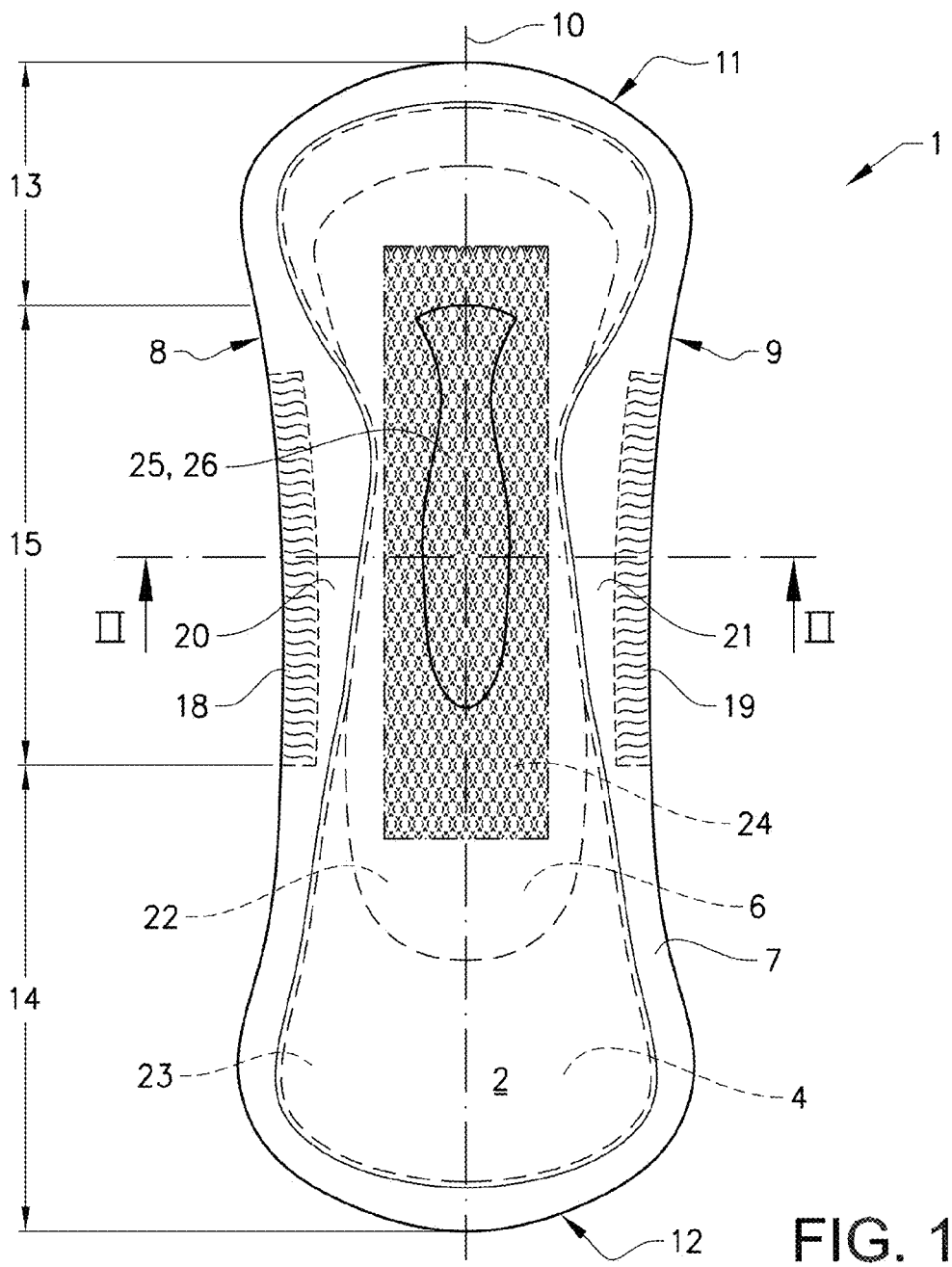
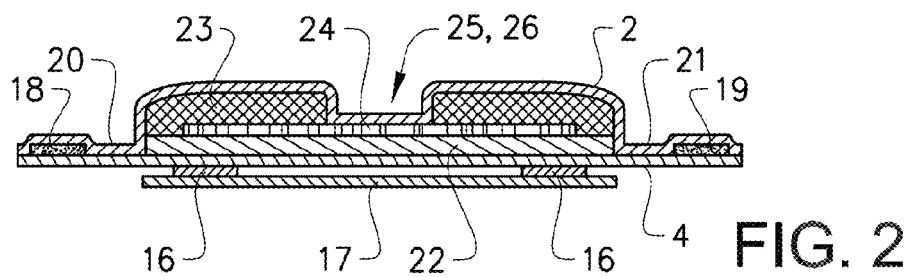

ABSORBENT ARTICLE HAVING FLUID FLOW CONTROL MEMBER

TECHNICAL FIELD

The present disclosure concerns a disposable absorbent article comprising a fluid flow control member.

BACKGROUND ART

Disposable absorbent articles for hygiene purposes are typically intended to absorb body liquids, such as urine and blood. Users put high demands on such articles, requiring them to be thin and comfortable and at the same time effectively absorb body liquids.

Disposable absorbent articles, such as sanitary napkins, diapers, incontinence guards or the like typically include a liquid pervious topsheet, intended to be facing the wearer during use, a liquid impervious backsheet and an absorbent structure there between. Absorbent structures commonly used are relatively thin and compressed, and often include a high amount of so called superabsorbents, which have a high absorption capacity but in many cases a too low absorption speed in order to instantaneously be able to absorb the large amount of liquid that can be discharged during a few seconds of urination. Therefore, a liquid acquisition layer is commonly incorporated in the absorbent article, which layer should be able to quickly receive large amounts of liquid and temporarily store it before the liquid is absorbed by the absorbent structure. An example of an absorbent article comprising a liquid acquisition layer is disclosed in WO 2009105000 A1.

It is also desirable that the absorbent article has sufficient liquid distributing capacity, in order to avoid leakage, and to fully use of the absorption capacity of the absorbent article.

When an absorbent article is used by a wearer, it is exposed to pressure, which tends to compress the article. Such pressures are typically about 2-5 kPa when standing or walking, about 10-20 kPa when sitting, 30 kPa when sitting and leaning forward, and up to 50 kPa when bicycling, in the centre of an absorbent pad. In order to maintain excellent liquid distribution properties in the absorbent article, it is desirable that the fluid flow control member can withstand high pressures.

There is a need for improvement of disposable absorbent hygiene articles in order to ensure fluid flow control, especially when the articles are exposed to pressure.

WO2005051656A1 discloses an incontinence article comprising a moisture management fabric composite in the form of a spacer fabric. Such fabric being constructed in order to be launderable, reusable and retain its qualities after repeated washings making it inexpedient for a disposable article.

SUMMARY OF THE DISCLOSURE

We have now successfully found that a fluid flow control member in the form of a novel spacer fabric having desired fluid flow control properties and pressure resistance may cost effectively be included in a disposable absorbent personal hygiene article. This is achieved by the absorbent article as defined in claim 1.

The present disclosure thus relates to an absorbent article, the absorbent article being a disposable personal hygiene article, comprising a liquid permeable top sheet, a liquid impermeable back sheet, and an absorbent core enclosed between the top sheet and the back sheet, and a fluid flow control member arranged between the topsheet and the backsheet, said fluid flow control member is a spacer fabric having a basis weight of 150-300 gsm and comprising a top layer and a bottom layer and an interconnecting layer of pile filaments between the top layer and the bottom layer, the pile filaments has a fineness of 80-130 dtex and the amount of pile filament connections is 50-150/cm$^2$.

BRIEF DESCRIPTION OF THE DRAWINGS

FIG. 1 shows an example of an absorbent article according to the disclosure, seen from the side which will be facing the user when it is being worn.

FIG. 2 shows a cross-sectional view of the absorbent article of FIG. 1, along the line II-II.

DETAILED DESCRIPTION OF THE DISCLOSURE

Figure 3:
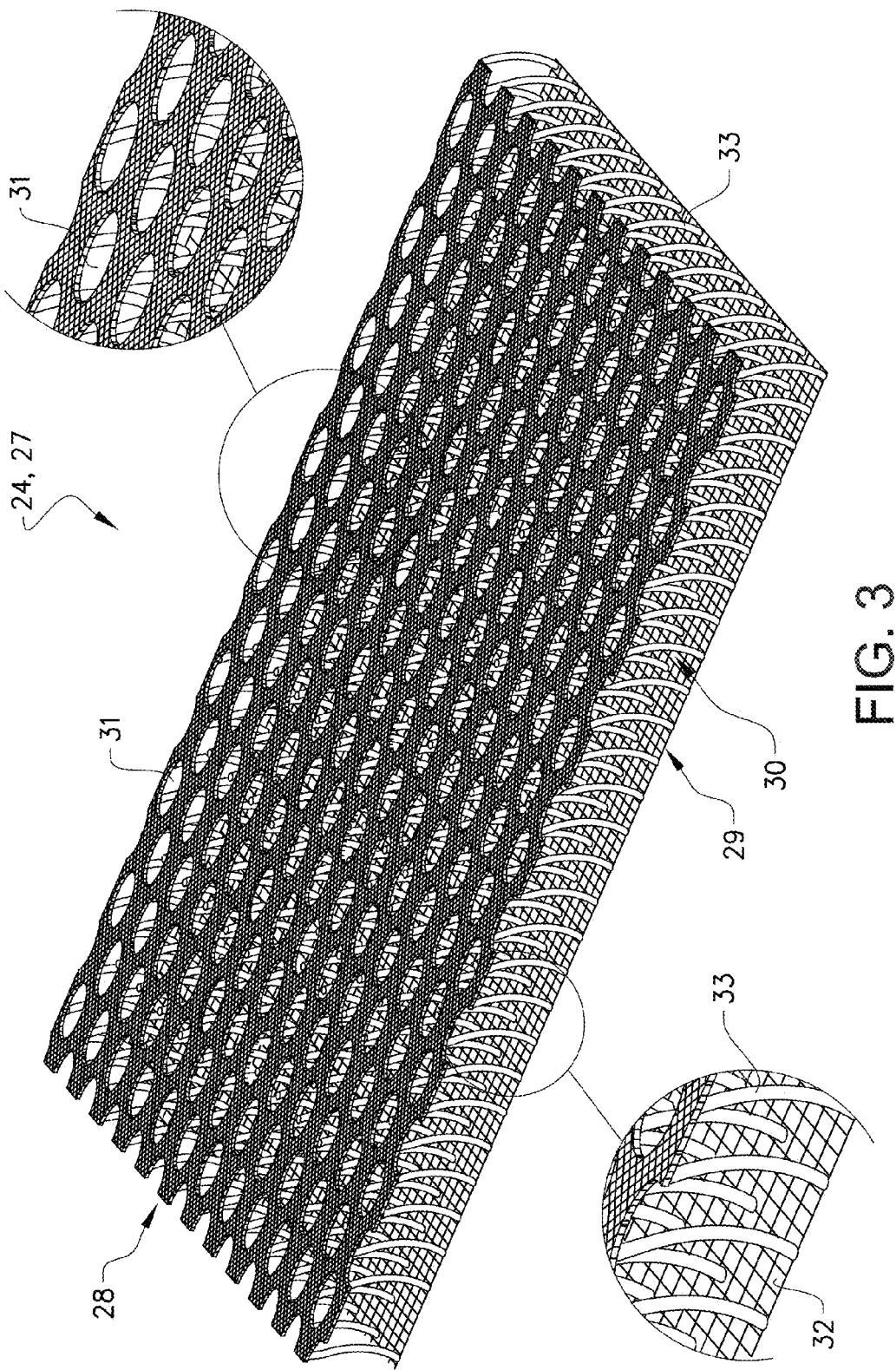
FIG. 3 shows a section through a fluid flow control member according to the disclosure.

The absorbent article of the disclosure, being a personal hygiene article may be any type of disposable absorbent personal hygiene article, such as incontinence protectors, sanitary napkins, panty liners, diapers with tape fasteners, pant diapers or belted diapers.

As used herein, the term "disposable" refers to articles which are intended to be discarded after a limited use and that are not intended to be laundered or otherwise restored for reuse.

The absorbent article comprises a liquid permeable topsheet, a liquid impermeable backsheet, and an absorbent core enclosed between the topsheet and the backsheet, and a fluid flow control member arranged between the topsheet and the backsheet. The fluid flow control member is a spacer fabric comprising a top layer and a bottom layer and an interconnecting layer of pile filaments between the top layer and the bottom layer. The top layer and the bottom layer of the spacer fabric may have different configurations in order to direct the speed of the flow of the liquid.

The fluid flow control member of the disclosure is more compression resistant than members that have previously been used for fluid flow control in disposable absorbent articles but at the same time have a relatively low surface weight due to its structure. This allows for a slim and efficient fluid flow control member that will maintain its structure and fluid flow control properties when pressure is exerted on it during use of the absorbent article. The spacer fabric may have a ratio of thickness to basis weight at 15 kPa of at least $1.5 \cdot 10^{-5}$ m/gsm and less than $2.5 \cdot 10^{-5}$ m/gsm, preferably less than $2.0 \cdot 10^{-5}$ m/gsm as measured according to the Mecano-method disclosed herein. "gsm" is used herein for g/m$^2$. The spacer fabric of the disclosure may have a ratio of thickness to basis weight of at least $1.5 \cdot 10^{-5}$ m/gsm at pressures below 20 kPa.

The spacer fabric has a basis weight of 150-300 gsm, preferably 150-250 gsm, more preferably 200-230 gsm.

The density of the pile filament connections and their dimension (in dtex) according to the disclosure is particularly suitable making the material soft but still able to withstand the exerted pressures during its use. The spacer fabric according to the disclosure expands immediately and almost completely after the removal of the compressive force exerted during its use. "Density" is herein used as a measure of the amount of pile filament connections per $cm^2$.

The interconnecting layer of pile filaments between the top layer and the bottom layer of the spacer fabric according to the disclosure have a fineness of 80-130 dtex, preferably 90-120 dtex and the density of pile filament connections is 50-150/$cm^2$, preferably 70-100/$cm^2$.

The pile filaments may together form channels, preferably in the diagonal direction, through the fabric in order to efficiently distribute liquid in the absorbent article.

The parameters of the material of the fluid flow control member of the disclosure, i.e. the spacer fabric, ensure a porous material in which a free volume is present, also when the absorbent article is exposed to pressure exerted by a user wearing the article, as a result of high resistance to compression. Due to the free volume the spacer fabric can accommodate and temporarily hold relatively large liquid volume. Thus, body liquids discharged can be effectively received into to the spacer fabric, and can flow inside it to different parts of the absorbent core, where it is absorbed, and accordingly the risk of leakage is minimised.

The top layer of the spacer fabric may have an open structure in order to ensure a rapid inflow and effective distribution of liquid. The openings of the top layer may have a longitudinal dimension of 3.0-4.5 mm and a transverse dimension of 1.5-3.0 mm. The shape of the openings may be circular to oval, but oval is preferred. The top layer may have 3-8, preferably 4-6 openings per $cm^2$. The bottom layer of the spacer fabric may have a more closer structure with relatively small openings. The bottom layer may have 50-150 openings per $cm^2$.

Suitably, the spacer fabric according to the disclosure has a total free volume of at least 20 ml, to ensure prevention of leakage. The spacer fabric advantageously has a thickness of 3-6 mm, preferably 3.5-5 mm at 1 kPa as measured according to DIN EN ISO 5084. The spacer fabric may have a width of less than 40 mm, such as 30-40 mm. The length of the member may be less than 150 mm, such as 120-150 mm.

The spacer fabric may for example have a size of about 30×120×5 mm to fit properly in the crotch area.

The spacer fabric is preferably substantially free from absorbing fibres and superabsorbent material.

The spacer fabric preferably comprises thermoplastic polymer fibres, preferably selected from but not limited to, polyesters, polyamides and polyolefins such as polyethylenes and polypropylenes, and may be a mixture of any of these. The material may also contain surfactant to facilitate liquid penetration in order to be drained quickly and not hold any liquid, thus maintaining free volume capacity for the next gush of liquid. For a preferred spacer fabric the yarns of the first and second layers as well as the pile filaments are of polyester.

The spacer fabric may have 5-15, preferably 8-12 courses/cm in the production direction of the fabric and 6-12, preferably 7-10 wales/cm in the cross direction of the fabric. The yarn of the top layer of the spacer fabric may have a fineness of 60-100 dtex. The yarn of the bottom layer of the spacer fabric may have a fineness of 90-130 dtex. The pile filaments may have a fineness of 80-130 dtex, preferably 90-120 dtex.

The spacer fabric may have an elongation, in a production direction, of less than 25%, preferably less than 15%, most preferably less than 10% at 10 N, preferably less than 15% at 5 N, as measured according to the Edana test method WSP 110.4 (05) Breaking Force and Elongation NW, for a successful convertion to a disposable absorbent article.

The spacer fabric is orientated in the absorbent product such that the top layer of the spacer fabric is facing the direction of the topsheet and the bottom layer of the spacer fabric is facing the direction of the backsheet.

The topsheet and the backsheet of the absorbent article may extend together laterally outside of the absorbent core along the whole circumference of the absorbent core and be connected to each other in an edge joint around the periphery of the absorbent core. The backsheet may preferably cover part of the topsheet to form an edge barrier. The edge joint may be formed in any suitable manner as known in the art such as by means of adhesive, ultrasonic bonding, thermobonding, stitching, etc. Alternative covering arrangements such as wrapped-around covers are also conceivable within the scope of the disclosure.

The topsheet may consist of any material which is suitable for the purpose, i.e. be soft and liquid pervious. Examples of commonly found topsheet materials are nonwoven materials, perforated plastic films, plastic or textile mesh, and fluid permeable foam layers. Laminates consisting of two or more topsheet materials are also commonly employed, as are top sheets consisting of different materials within different parts of the fluid permeable wearer-facing surface.

The backsheet is fluid impermeable. However, backsheet materials that are only fluid repellant may be used particularly in instances where relatively small amounts of urine are expected to be taken up. The backsheet is commonly constituted by a thin, flexible, fluid-impermeable plastic film, but fluid-impermeable nonwoven materials, fluid impermeable foams and fluid impermeable laminates are also contemplated within the scope of the disclosure. The backsheet may preferably be breathable, implying that air and vapor may pass through the backsheet. Furthermore, the backsheet may have an outer, garment-facing surface of a textile material such as nonwoven.

The absorbent core may be made up of any suitable absorbent or fluid uptake material as known in the art, such as one or more layers of cellulose fluff pulp, foam, fibre waddings, etc. The absorbent core may contain fibers or particles of highly absorbent polymer material, commonly known as superabsorbents, which are materials having the ability to absorb and retain large quantities of fluid upon formation of a hydrogel. The superabsorbents may be mixed with cellulose fluff pulp and/or may be arranged in pockets or layers in the absorbent core. The fibres may be pulp fibres and the superabsorbent material may be polyacrylate-based particles. An absorbent structure may comprise 40-80% superabsorbents and 60-20% pulp fibres.

The absorbent core may further incorporate components for improving the properties of the absorbent core. Some examples of such components are binder fibers, fluid-dispersing materials, wetness indicators etc., as known in the art.

The absorbent article typically, in case of a pad or a sanitary napkin, has an elongate, generally rectangular shape when fully extended in all directions. In this context, a generally rectangular shape is intended to encompass also that, for instance, the corners of the absorbent article may be rounded, or that the edges of the absorbent article may not be completely linear. Accordingly, any suitable shape may be used for the absorbent article, such as hourglass shape, trapezoidal shape, triangular shape an oval shape, etc., The shape of the article of the disclosure may be symmetrical about a transverse center line through the article, or may be asymmetrical with end portions having differing shapes and/or differing sizes.

The absorbent article may have two longitudinal side edges having equal length and extending generally in the same direction as a longitudinal center line through the absorbent article. Front and rear end edges typically extend transversely to the longitudinal center line at the ends of the absorbent article. The rear end edge is intended to be orientated rearwards during use of the absorbent article, and the front end edge is intended to be facing forwards towards the abdomen of the wearer.

The absorbent article may have a front end portion, a rear end portion and a crotch portion located intermediate the end portions, the crotch portion being a portion, which is intended to be placed against the crotch of a wearer during use of the article and to constitute the main acquisition area for body fluid that reaches the absorbent article.

The absorbent article may further include fastening means for fastening of the absorbent article inside a supporting pant garment, such as a pair of underpants. The fastening means may be in the form of two longitudinally extending bands of pressure sensitive adhesive arranged on the garment-facing surface of the backsheet. The fastening means can be covered by a releasable protective layer, e.g. a siliconized paper, a nonwoven or any other releasable material as is known in the art. Before placing the absorbent article in the supporting pant garment, the protective layer is removed from the fastening means to expose the adhesive and make it available for fastening to the pant garment.

Elastic elements may be arranged along the side edges laterally outside the absorbent core. The elastic elements may be bands of elastic material. The elastic elements are optional components of the absorbent article of the disclosure and may be omitted.

The fastening means is optional to the disclosure and may be omitted, if desired. When using an adhesive fastening means, any suitable adhesive pattern may be used such as full coating of the backsheet, one or more longitudinal adhesive band, transverse bands, dots, circles, curves, stars, etc. Furthermore, the fastening means may be a mechanical fastener such as hook-type fasteners, clips, press studs, etc. or may be a frictional fastener such as a frictional coating or an open-celled foam. Combinations of different types of fasteners are also conceivable.

The fluid control member may be situated above or below an absorbent core, but preferably above an absorbent core. The absorbent core of the absorbent article preferably comprises a first absorbent layer and a second absorbent layer. The fluid flow control member may be arranged in the absorbent article between the first absorbent layer and the second absorbent layer. The first absorbent layer may be placed beneath and in direct contact with the topsheet, or may alternatively be placed in indirect contact with the topsheet through one or more intervening components such as nonwoven layers or further absorbent layers. Similarly, the second absorbent layer may be placed directly beneath the fluid flow control member and in direct contact with the fluid flow control member and the backsheet, or may be in indirect contact with one or both of those components by intervening components. By arranging the fluid flow control member between the first and second absorbent layers, it forms a channel in the absorbent article and leads the fluid to the back and front of the article. The contact area between the fluid flow control member and the absorbent core increases which facilitates distribution and rapid absorption of liquid in the article.

The absorbent layers may be homogeneous structures or may in themselves be layered structures such as absorbent laminates of the same or different materials. The absorbent layers may have uniform thickness or may vary in thickness in different parts of the layers. Similarly, the basis weight and composition may vary within the absorbent layers. By way of example, an absorbent layer may comprise a mixture of absorbent and/or non-absorbent fibres and superabsorbent material, wherein the ratio of superabsorbent material to fibres may vary in the layer.

The first and second absorbent layers may have any suitable shape, such as an hourglass shape with widened end portions and a narrow portion in the crotch portion, or a rectangular shape. The second absorbent layer may be placed beneath the first absorbent layer and may be somewhat smaller than the first absorbent layer. The first absorbent layer may extend further forward and rearward in the absorbent article than the second absorbent layer. Moreover, the second absorbent layer may be omitted in the absorbent article according to the disclosure or the article may comprise one or more further absorbent layers.

The first absorbent layer advantageously has an opening extending completely through the layer in the crotch portion of the absorbent article, thereby forming a cavity in the article. The opening preferably has elongate shape, approximately mimicking the shape of the absorbent layers.

In case of an opening in the absorbent layer the topsheet may extend down into the cavity that is defined by the opening in the first absorbent layer and the surface of the fluid flow control structure that is facing the topsheet. Thereby, the cavity will be lined with topsheet material and will be accessible from the outer body facing surface of the absorbent article. The cavity is advantageously located in the wetting area of the absorbent article and will then in use be placed directly beneath the urethra and the vaginal opening of a female wearer. Accordingly, any body fluid that is released to the absorbent article will flow into the cavity and be distributed further into and throughout the absorbent core. A part of the fluid that is collected in the cavity may be absorbed by the first absorbent layer through the walls of the cavity. However, the major part of the fluid will continue downward in the absorbent article, through the bottom of the cavity and into the fluid flow control member where it is distributed longitudinally and laterally along the flow control member.

The fluid flow control member may be of rectangular shape and may be surrounded in the longitudinal and lateral directions by portions of the absorbent core. Other shapes and configurations for the fluid flow control structure may also be used. However, it is generally advantageous if the fluid flow control member has smaller width and is shorter than the absorbent core, as this facilitates distribution to a large area of the absorbent core.

The disclosure will now be described by means of example referring to FIGS. 1-3. In this example of the disclosure the absorbent article is a urine incontinence protector 1 in the form of a sanitary napkin or pad. In FIG. 1, the absorbent article is seen from the side of the absorbent article that is intended to be facing towards a wearer's body when being worn, and in FIG. 2, it is seen in cross-section along the line II-II in FIG. 1. The absorbent article 1 comprises a fluid permeable topsheet 2, disposed at the top surface of the absorbent article 1 which is intended to be facing a wearer of the absorbent article 1, a fluid impermeable backsheet 4 disposed at the lower back side of the incontinence protector 1 that is intended to be facing the undergarment of the wearer, and an absorbent core 6, enclosed between the topsheet 2 and the backsheet 4.

The topsheet 2 and the backsheet 4 of the incontinence protector 1 extend together laterally outside of the absorbent core 6 along the whole circumference of the absorbent core 6 and are connected to each other in an edge join 7 around the periphery of the absorbent core 6. The two longitudinal side edges 8, 9 of the absorbent article have equal length and extend generally in the same direction as a longitudinal centre line 10 through the absorbent article 1. Front and rear end edges 11, 12 extend transversely to the longitudinal centre line 10 at the ends of the incontinence protector. The incontinence protector 1 has a front end portion 13, a rear end portion 14 and a crotch portion 15 located intermediate the end portions 13, 14, the crotch portion 15 being intended to be placed against the crotch of a wearer during use and to constitute the main acquisition area for body fluid that reaches the absorbent article 1.

The incontinence protector 1 may further include fastening means 16 for fastening of the incontinence protector 1 inside a supporting pant garment, such as a pair of underpants. The fastening means 16 is in the form of two longitudinally extending bands of pressure sensitive adhesive arranged on the garment-facing surface of the backsheet 4. In FIG. 2, the fastening means 16 can be seen to be covered by a releasable protective layer 17. Elastic elements 18, 19 in the form of bands of elastic material may also be arranged along the side edges 8, 9 in the side flaps 20, 21 formed by portions of the topsheet 2 and backsheet 4 extending laterally outside the absorbent core 6 to improve the anatomical fit of the incontinence protector.

The absorbent core 6 comprises a first absorbent layer 23 and a second absorbent layer 22. A fluid flow control member 24 is arranged between the first absorbent layer 23 and the second absorbent layer 22. In this example, the first absorbent layer 23 is placed beneath and in direct contact with the topsheet 2.

The first absorbent layer 23 has an opening 25 extending completely through the absorbent layer 23 in the crotch portion 15 of the incontinence protector 1. The opening 25 has an elongate shape. The topsheet 2 extends down into the cavity 26 that is defined by the opening 25 in the first absorbent layer 23 and the topsheet-facing surface of the fluid flow control member 24. The cavity 26 is located in the wetting area of the incontinence protector 1 and will in use be placed directly beneath the urethra and the vaginal opening of a female wearer. Any body fluid that is released to the incontinence protector 1 will directly flow into the cavity 26 and be distributed further into and throughout the absorbent core 6 via the fluid control member 24.

The fluid flow control member in the form of a spacer fabric 27 is shown in FIG. 3. The spacer fabric 27 has a top layer 28 and a bottom layer 29 and a connecting layer 30 of pile filaments 33 between the top layer 28 and the bottom layer 29. The top layer 28 has larger openings 31 than the bottom layer 29 having comparable small openings 32.

An example of a spacer fabric of the disclosure may have a the following properties: a surface weight of the spacer fabric of about 250 gsm, a thickness of about 0.5 cm, yarn of the top layer about 76 dtex, yarn of the bottom layer about 110 dtex, pile filaments 108 dtex, pile connections about 72-95/cm², openings in top layer about 5 per cm², about 10 courses/cm and about 8 wales/cm.

Experiments

A number of different materials have been compression tested, to compare the strain of commonly used liquid acquisition distribution materials, being high lofts of air through bonded nonwoven, with materials used for the fluid flow control member of the present disclosure. These tests were performed by the methods as described here below.

Strain (Mecano-Method)

Procedure:

The principle of the method is to slowly compress a material with a metal rod to a force of 5 N while continuously measuring the thickness of the material. The result consists of the data points for force and extension. The force translates to a pressure given the contact area of the rod. The metal rod is cylindrical and has a diameter of 10 mm with a flat base having a diameter >7 cm. The rod is mounted in a 10 N load cell in the upper fixture of an Instron testing apparatus. A flat plate is mounted in the bottom fixture and is centred under the rod to that a sample may be placed on top of the plate and be compressed without movement of the plate. The rate of movement of the rod is 5 mm per minute. These settings have been pre-programmed into an Instron Bluehill program called "New Mecano 5 N", but before running a test, the program settings should be checked in order to make sure that all limits are set to their proper values. Running with a modified version could lead to damage to the equipment, especially the sensitive load cell.

Running a Test:

The first run is an empty run without a sample. This run is used to find the zero thickness position, which is where the steel plate stops the rod. The empty run typically generates forces higher than the maximum limit set before the rod stops, because of the rapid increase in force that occurs when the rod impacts the metal and for which the apparatus cannot compensate sufficiently quickly. Care should be taken to ascertain that the load cell can withstand the impact without being damaged. Special settings can be used for the empty run to lower the limiting maximum force and the speed of the rod.

When the rod stops, the Instron equipment awaits user input. The extension is then manually reset to zero. This ensures that the extension is set to zero at the exact correct point where the rod touches the base and the extension is measured relative to the bottom plate. The rod may thereafter be manually moved up so that a sample can be placed on the lower plate.

To test a sample, the rod is moved manually so that it is above the surface of the sample and the program is started. The rod moves down at a speed of 5 mm per minute until the limiting force is reached.

Samples:

The samples are squares with 50 mm sides punched from the tested material. Samples were taken, if the material was of uneven thickness, from the thickest parts of the material. The rod is pressed into the centre of the sample and each sample is tested three times without being moved between runs. Ten samples of each tested material are used, giving thirty measurements in total including the empty run, thirty-one test runs are made for each tested material.

The Tested Materials Were:

| Sample | Surface weight (gsm) | Thickness at 1 kPa* (mm) | Pile filaments (dtex) | Pile connections/cm² |
|---|---|---|---|---|
| Disclosure | 230 | 4.16 | 108 | 84 |
| B) 5683; Müller Textil GmbH | 230 | 3.16 | 33 | 395 |

-continued

| Sample | Surface weight (gsm) | Thickness at 1 kPa* (mm) | Pile filaments (dtex) | Pile connections/ cm$^2$ |
|---|---|---|---|---|
| C) 15-307 nw highloft; Libeltex | 100 | 1.85 | — | — |
| D) SF 0908P700160 Wellcool | 700 | 6.94 | n.i. | n.i. |

*as measured according to the Mecano-menthod disclosed herein.
n.i.—no information Results:

The result is the complete set of data points for force versus extension. The force is recalculated into pressure using the force (in N), measured in Mecano, divided by the bottom area (in m$^2$) of the rod.

The ratio of thickness to basis weight in m/gsm has been calculated by dividing the thickness measured in Mecano (in m) with the surface weight (in gsm) of the used material.

Figure 4:
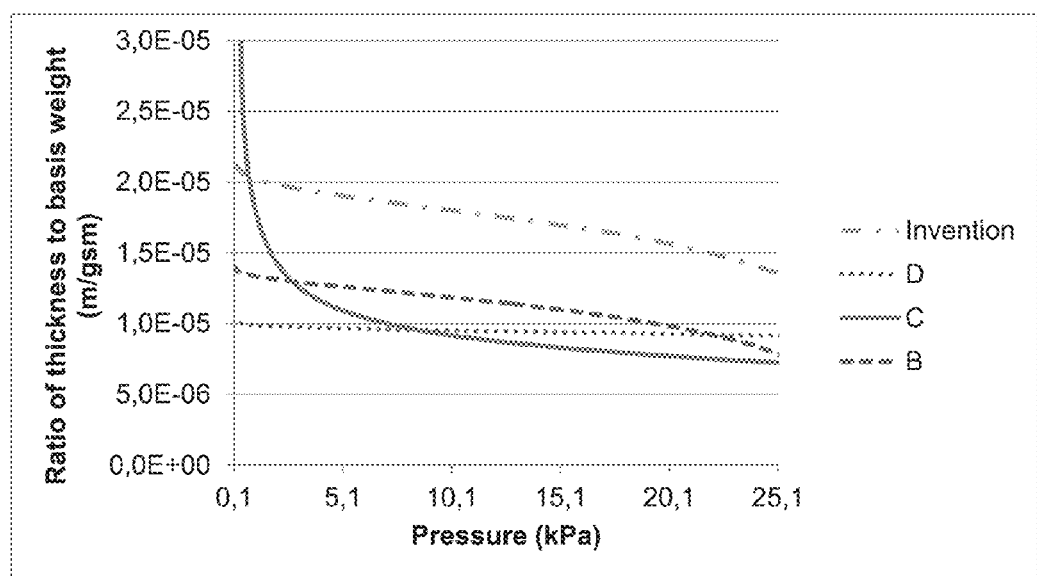
FIG. 4 shows a graph of the ratio of the thickness to basis weight at different pressures for different types of liquid distribution structures.

The calculated values of pressure (in kPa) and ratio of thickness to basis weight (in m/gsm) for the different samples are plotted in a graph, as shown in FIG. 4. The calculated values of pressure (in kPa) and ratio of thickness to basis weight (in m/gsm) for the different samples are plotted in a graph, as shown in FIG. 4. The figure shows that a high ratio is maintained at the different pressures for the fluid flow control member of the disclosure. The spacer fabric of the disclosure has a ratio of thickness to basis weight of at least $1.5 \cdot 10^{-5}$ m/gsm at pressures below 20 kPa.

Tensile Testing

Procedure:

Tensile testing measurements of a spacer fabric according to the disclosure and sample B were made according to the Edana test method WSP 110.4 (05) Breaking Force and Elongation NW or the American Standard method ASTMD 882 (equivalent methods). The used INSTRON machine was id: 100180; cell 100N id:100182. The test samples were 25 mm wide and the used pulling speed on the Instron was 100 mm/min.

Figure 5:
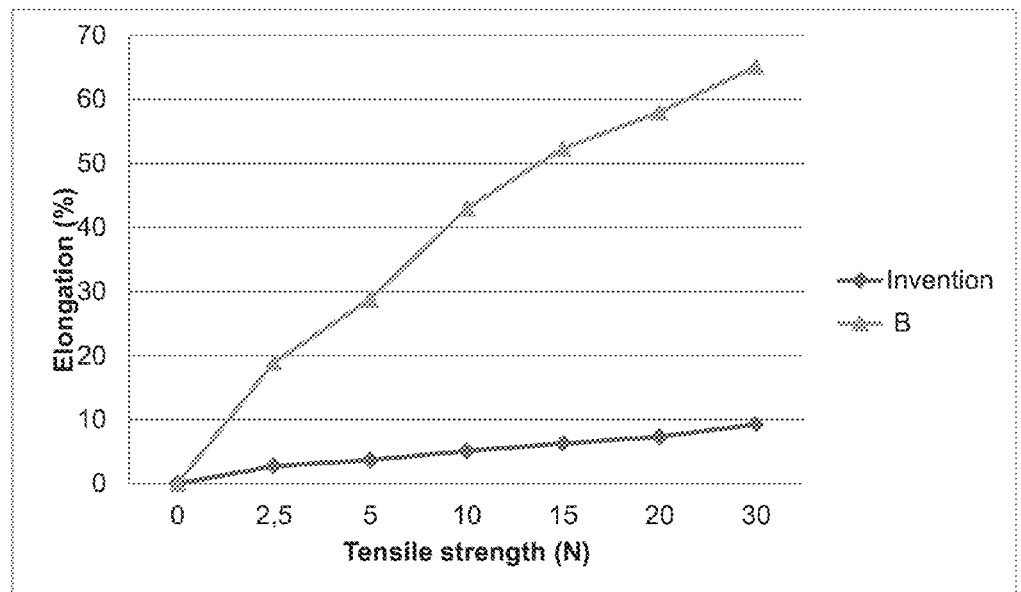
FIG. 5 shows a graph of the elongation (%) for two types of liquid distribution structures at different tensile strengths (N).

Results:

The values of tensile strength (in N) and elongation (in %) for the two samples are plotted in a graph, as shown in FIG. 5. The spacer fabric according to the disclosure shows a low % elongation making it expedient for convertion in manufacturing machines into a disposable absorbent article.

The invention claimed is:

1. An absorbent article, the absorbent article being a disposable personal hygiene article, comprising a liquid permeable top sheet, a liquid impermeable back sheet, an absorbent core enclosed between the top sheet and the back sheet, and a fluid flow control member arranged between the top sheet and the back sheet, wherein said fluid flow control member is a spacer fabric having a basis weight of 150-300 gsm and comprising a top layer, a bottom layer and an interconnecting layer of pile filaments between the top layer and the bottom layer, the pile filaments have a fineness of 80-130 dtex and the density of pile filament connections is 50-150 per cm$^2$ and the absorbent core comprises superabsorbent polymers.

2. The absorbent article according to claim 1, wherein the pile filaments have a fineness of 90-120 dtex.

3. The absorbent article according to claim 1, wherein the density of pile filament connections is 70-100/cm$^2$.

4. The absorbent article according to claim 1, wherein the spacer fabric has a ratio of thickness to basis weight at 15 kPa of at least $1.5 \cdot 10^{-5}$ m/gsm, as measured according to the Mecano-method disclosed herein.

5. The absorbent article according to claim 1, wherein the spacer fabric has a ratio of thickness to basis weight at 15 kPa of less than $2.5 \cdot 10^{-5}$ m/gsm as measured according to the Mecano-method disclosed herein.

6. The absorbent article according to claim 1, wherein said spacer fabric has a basis weight of 150-250 gsm.

7. The absorbent article according to claim 1, wherein said spacer fabric has a thickness of 3-6 mm at 1 kPa as measured according to DIN EN ISO 5084.

8. The absorbent article according to claim 1, wherein the top layer and the bottom layer of the spacer fabric have different configurations.

9. The absorbent article according to claim 1, wherein openings in the top layer of the spacer fabric have a longitudinal dimension of 3.0-4.5 mm and a transverse dimension of 1.5-3.0 mm.

10. The absorbent article according to claim 1, wherein the top layer of the spacer fabric has 3-8 openings per cm$^2$.

11. The absorbent article according to claim 1, wherein the bottom layer of the spacer fabric has 50-150 openings per cm$^2$.

12. The absorbent article according to claim 1, wherein the spacer fabric has 5-15 courses/cm in a production direction of the fabric and 6-12 wales/cm in a cross direction of the fabric.

13. The absorbent article according to claim 1, wherein the spacer fabric in a production direction has an elongation of less than 25% at 10 N, as measured according to the Edana test method WSP 110.4 (05) Breaking Force and Elongation NW.

14. The absorbent article according to claim 1, wherein the spacer fabric is located between the topsheet and the absorbent core.

15. The absorbent article according to claim 1, wherein the absorbent core comprises a first absorbent core layer and a second absorbent core layer, and wherein said spacer fabric is located between said first and second absorbent core layers.

16. The absorbent article of claim 15, wherein said first absorbent core layer is arranged between the top sheet and the second absorbent core layer, said first absorbent core layer have an opening extending through the first absorbent core layer.

17. The absorbent article according to claim 1, wherein the spacer fabric has: (i) a ratio of thickness to basis weight at 15 kPa of less than $2.0 \cdot 10^{-5}$ m/gsm as measured according to the Mecano-method disclosed herein, (ii) a basis weight of 150-250 gsm, (iii) a thickness of 3.5-5 mm at 1 kPa as measured according to DIN EN ISO 5084, (iv) 8-12 courses/cm in a production direction of the fabric or 7-10 wales/cm in a cross direction of the fabric, or (v) an elongation in a production direction of less than 15% at 5 N, as measured according to the Edana test method WSP 110.4 (05) Breaking Force and Elongation NW.

18. The absorbent article according to claim 1, wherein the top layer of the spacer fabric has 4-6 openings per cm$^2$.

19. The absorbent article according to claim 1, wherein the spacer fabric has a basis weight of 200-230 gsm.

* * * * *